US006866685B2

(12) United States Patent
Chan et al.

(10) Patent No.: US 6,866,685 B2
(45) Date of Patent: *Mar. 15, 2005

(54) PROSTHETIC JOINTS HAVING REDUCED AREA BEARING SURFACES AND APPLICATION THEREOF TO A RANGE OF SIZES OF PROSTHETIC JOINTS

(75) Inventors: Frank W. Chan, Warsaw, IN (US); Jorge A. Ochoa, Fort Wayne, IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/643,039

(22) Filed: Aug. 18, 2003

(65) Prior Publication Data

US 2004/0034433 A1 Feb. 19, 2004

Related U.S. Application Data

(63) Continuation of application No. 10/025,945, filed on Dec. 19, 2001, now Pat. No. 6,660,040.

(51) Int. Cl.[7] .................................................. A61F 2/32
(52) U.S. Cl. .................................. 623/22.21; 623/22.17
(58) Field of Search .......................... 623/22.21, 22.11, 623/22.15, 22.17

(56) References Cited

U.S. PATENT DOCUMENTS 5,916,269 A   6/1999   Serbousek et al.

Primary Examiner—Cary E. O'Connor
Assistant Examiner—Candice C. Stokes
(74) Attorney, Agent, or Firm—Maginot, Moore & Beck

(57) ABSTRACT

A prosthetic component is configured to have intentional interruptions in an articulating face thereof. The intentional interruptions are configured to yield an optimum contact area or bearing surface, particularly with regard to low wear and greater lubricity through the application of lubrication and contact mechanics theory for the particular prosthetic component. Such optimization is applied to a wide range of prosthetic component sizes of the particular prosthetic component. The optimum range of percentage area of relief or interruptions, defined as a percentage of a baseline uninterrupted bearing surface area to be removed by the features of the interrupted bearing surface configuration is from 0.3% to 73.7% for hard-on-hard bearing components and from 5.7% to 83.2% for polyethylene-on-hard bearing components. The range for both hard-on-hard and polyethylene-on-hard implants translates to a relieved area ranging from 0.3% to 31.9% of the area of the entire articulating surface, depending on the size of the implant. For both hard-on-hard and polyethylene-on-hard bearing combinations, optimally decreasing the contact area or bearing surface by interruptions in the articulating surfaces will allow for the benefits of larger diameter prosthetic components with an increased range of motion and decreased potential for dislocation, and the low frictional torques and lower wear of smaller diameter components.

13 Claims, 11 Drawing Sheets

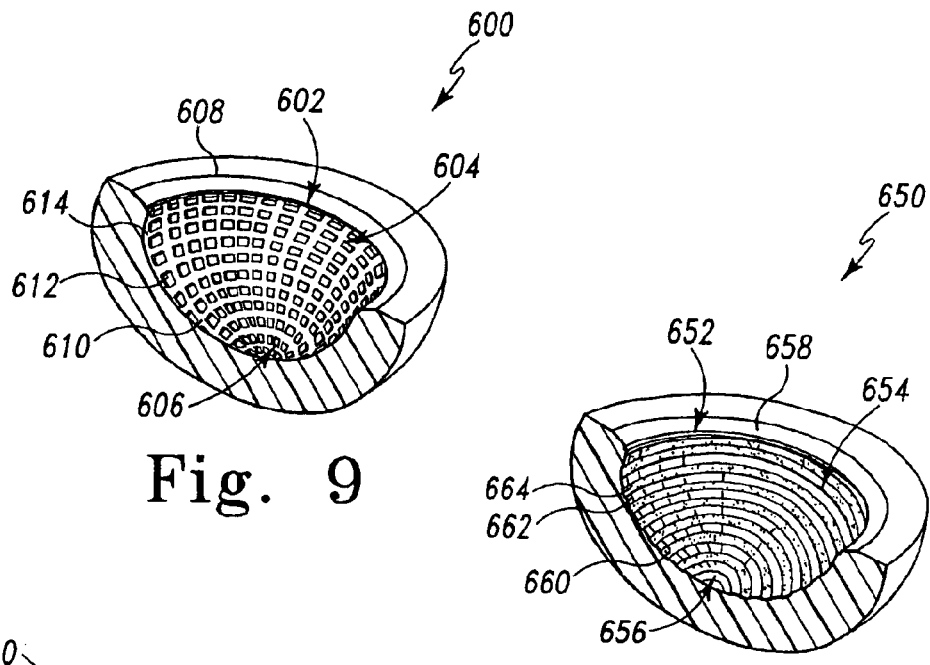
Fig. 9
Fig. 10
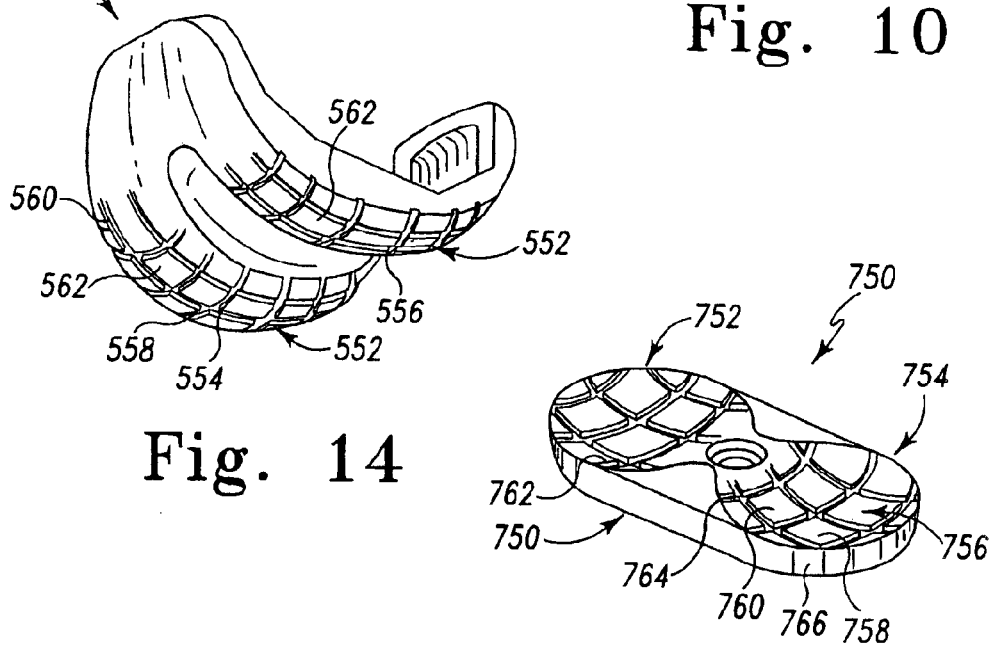
Fig. 14
Fig. 15

Fig. 18

CERAMIC ON CERAMIC

| φnominal (mm) | 40 μm | | | 60 μm | | | 80 μm | | | 100 μm | | | 120 μm | | |
|---|---|---|---|---|---|---|---|---|---|---|---|---|---|---|---|
| | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) |
| 22 | 42.43 | 0.0 | 0.00 | 32.40 | | | 26.76 | | | 23.08 | | | 20.45 | | |
| 23 | 45.02 | 5.7 | 0.31 | 34.38 | | | 28.39 | | | 24.48 | | | 21.69 | | |
| 24 | 47.65 | 10.9 | 0.58 | 36.38 | | | 30.05 | | | 25.91 | | | 22.96 | | |
| 25 | 50.31 | 15.7 | 0.80 | 38.41 | | | 31.73 | | | 27.36 | | | 24.24 | | |
| 26 | 53.01 | 20.0 | 1.00 | 40.47 | | | 33.43 | | | 28.82 | | | 25.54 | | |
| 27 | 55.74 | 23.9 | 1.18 | 42.56 | | | 35.15 | | | 30.31 | | | 26.85 | | |
| 28 | 59.51 | 27.5 | 1.31 | 44.67 | 0.3 | 0.01 | 36.89 | | | 31.81 | | | 28.18 | | |
| 29 | 61.31 | 30.8 | 1.43 | 46.81 | 5.0 | 0.18 | 38.66 | | | 33.33 | | | 29.53 | | |
| 30 | 64.14 | 33.8 | 1.54 | 48.97 | 9.4 | 0.33 | 40.44 | | | 34.87 | | | 30.89 | | |
| 31 | 67.01 | 36.7 | 1.63 | 51.16 | 13.4 | 0.46 | 42.25 | | | 36.42 | | | 32.27 | | |
| 32 | 69.90 | 39.3 | 1.71 | 53.37 | 17.1 | 0.58 | 44.07 | | | 38.00 | | | 33.66 | | |
| 33 | 72.83 | 41.7 | 1.78 | 55.60 | 20.5 | 0.68 | 45.92 | 3.7 | 0.10 | 39.59 | | | 35.07 | | |
| 34 | 75.78 | 44.0 | 1.84 | 57.86 | 23.7 | 0.77 | 47.78 | 7.5 | 0.20 | 41.19 | | | 36.49 | | |
| 35 | 78.77 | 46.1 | 1.89 | 60.13 | 26.7 | 0.85 | 49.66 | 11.2 | 0.29 | 42.81 | | | 37.93 | | |
| 36 | 81.78 | 48.1 | 1.94 | 62.43 | 29.4 | 0.92 | 51.56 | 14.6 | 0.38 | 44.45 | | | 39.37 | | |
| 37 | 84.82 | 50.0 | 1.97 | 64.76 | 32.0 | 0.98 | 53.47 | 17.7 | 0.45 | 46.10 | | | 40.84 | | |
| 38 | 87.89 | 51.7 | 1.99 | 67.10 | 34.5 | 1.04 | 55.41 | 20.6 | 0.51 | 47.77 | 0.9 | 0.02 | 42.31 | | |
| 39 | 90.99 | 53.4 | 2.00 | 69.46 | 36.8 | 1.09 | 57.36 | 23.4 | 0.57 | 49.45 | 4.5 | 0.10 | 43.80 | | |
| 40 | 94.11 | 54.9 | 2.03 | 71.84 | 38.9 | 1.13 | 59.33 | 26.0 | 0.62 | 51.14 | 8.0 | 0.17 | 45.30 | | |
| 41 | 97.26 | 56.4 | 2.06 | 74.25 | 40.9 | 1.17 | 61.31 | 28.5 | 0.67 | 52.85 | 11.2 | 0.24 | 46.82 | | |
| 42 | 100.43 | 57.8 | 2.08 | 76.67 | 42.9 | 1.20 | 63.31 | 30.8 | 0.71 | 54.58 | 14.2 | 0.29 | 48.34 | 0.01 | 0.01 |
| 43 | 103.63 | 59.1 | 2.09 | 79.11 | 44.7 | 1.24 | 65.32 | 33.0 | 0.75 | 56.31 | 17.0 | 0.35 | 49.88 | 3.8 | 0.07 |
| 44 | 106.86 | 60.3 | 2.11 | 81.57 | 46.4 | 1.26 | 67.36 | 35.0 | 0.79 | 58.06 | 19.7 | 0.39 | 51.43 | 6.9 | 0.12 |
| 45 | 110.10 | 61.5 | 2.12 | 84.05 | 48.0 | 1.29 | 69.40 | 36.9 | 0.82 | 59.83 | 22.3 | 0.44 | 53.00 | 9.1 | 0.17 |
| 46 | 113.38 | 62.6 | 2.13 | 86.55 | 49.5 | 1.31 | 71.46 | 38.7 | 0.85 | 61.60 | 24.6 | 0.48 | 54.57 | 12.5 | 0.21 |
| 47 | 116.67 | 63.6 | 2.14 | 89.06 | 51.0 | 1.33 | 73.54 | 40.5 | 0.87 | 63.39 | 26.9 | 0.51 | 56.15 | 17.5 | 0.25 |
| 48 | 119.99 | 64.6 | 2.15 | 91.60 | 52.4 | 1.34 | 75.63 | 42.3 | 0.90 | 65.20 | 29.1 | 0.55 | 57.75 | 19.8 | 0.29 |
| 49 | 123.34 | 65.6 | 2.15 | 94.15 | 53.7 | 1.36 | 77.74 | 43.9 | 0.92 | 67.01 | 31.1 | 0.58 | 59.36 | 22.0 | 0.32 |
| 50 | 126.70 | 66.5 | 2.15 | 96.72 | 54.9 | 1.37 | 79.86 | 45.4 | 0.94 | 68.84 | 33.1 | 0.60 | 60.98 | 24.2 | 0.35 |
| 51 | 130.09 | 67.4 | 2.15 | 99.31 | 56.1 | 1.38 | 82.00 | 46.9 | 0.95 | 70.68 | 34.9 | 0.63 | 62.61 | 26.1 | 0.39 |
| 52 | 133.50 | 68.2 | 2.15 | 101.91 | 57.3 | 1.39 | 84.15 | 48.3 | 0.97 | 72.53 | 36.7 | 0.65 | 64.25 | 28.1 | 0.43 |
| 53 | 136.94 | 69.0 | 2.14 | 104.53 | 58.4 | 1.40 | 86.31 | 49.6 | 0.98 | 74.40 | 38.4 | 0.67 | 65.90 | 29.7 | 0.45 |
| 54 | 140.39 | 69.8 | 2.14 | 107.16 | 59.4 | 1.41 | 88.48 | 50.8 | 0.99 | 76.27 | 40.0 | 0.69 | 67.56 | 31.7 | 0.47 |
| 55 | 143.87 | 70.5 | 2.13 | 109.82 | 60.4 | 1.41 | 90.67 | 52.0 | 1.01 | 78.16 | 41.5 | 0.71 | 69.23 | 33.4 | 0.49 |
| 56 | 147.36 | 71.2 | 2.13 | 112.49 | 61.4 | 1.42 | 92.88 | 53.2 | 1.02 | 80.06 | 43.0 | 0.72 | 70.91 | 35.0 | 0.51 |
| 57 | 150.88 | 71.9 | 2.12 | 115.17 | 62.3 | 1.42 | 95.09 | 54.3 | 1.02 | 81.97 | 44.4 | 0.74 | 72.60 | 36.5 | 0.53 |
| 58 | 154.42 | 72.5 | 2.12 | 117.87 | 63.2 | 1.43 | 97.32 | 55.4 | 1.03 | 83.89 | 45.7 | 0.75 | 74.31 | 38.0 | 0.54 |
| 59 | 157.98 | 73.1 | 2.11 | 120.59 | 64.0 | 1.43 | 99.57 | 56.4 | 1.04 | 85.82 | 47.0 | 0.76 | 76.02 | 39.4 | 0.55 |
| 60 | 161.56 | 73.7 | 2.11 | 123.32 | 64.8 | 1.43 | 101.82 | 57.4 | 1.05 | 87.77 | 48.2 | 0.77 | 77.74 | 40.8 | 0.57 |

BASELINE CONTACT AREA
MINIMUM % AREA OF RELIEF (COMPARED WITH UNINTERRUPTED BEARING SURFACE)
MINIMUM % AREA OF RELIEF (COMPARED WITH TOTAL ARTICULAR SURFACE)
MAXIMUM % AREA OF RELIEF (COMPARED WITH UNINTERRUPTED BEARING SURFACE)
MAXIMUM % AREA OF RELIEF (COMPARED WITH TOTAL ARTICULAR SURFACE)

Fig. 20

COBALT CHROMIUM ON POLYETHYLENE

| Φ(NOMINAL) (mm) | 300 μm | | | 400 μm | | | 500 μm | | | 600 μm | | |
|---|---|---|---|---|---|---|---|---|---|---|---|---|
| | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) | AREA (mm²) | % AREA OF RELIEF (OF UNINTERRUPTED CONTACT AREA) | % AREA OF RELIEF (OF TOTAL ARTICULAR SURFACE AREA) |
| 22 | 504.69 | 36.4 | 24.19 | 417.85 | 23.2 | 12.77 | 361.17 | 11.2 | 5.31 | 320.78 | 0.0 | 0.00 |
| 23 | 535.29 | 40.1 | 25.82 | 443.14 | 27.6 | 14.73 | 382.97 | 16.2 | 7.49 | 340.10 | 5.7 | 2.33 |
| 24 | 566.34 | 43.4 | 27.14 | 468.79 | 31.6 | 16.36 | 405.09 | 20.8 | 9.32 | 359.71 | 10.8 | 4.30 |
| 25 | 597.83 | 46.3 | 28.22 | 494.80 | 35.2 | 17.73 | 427.52 | 25.0 | 10.87 | 379.58 | 15.5 | 5.99 |
| 26 | 629.73 | 49.1 | 29.10 | 521.15 | 38.4 | 18.87 | 450.25 | 28.8 | 12.19 | 399.72 | 19.7 | 7.43 |
| 27 | 662.04 | 51.5 | 29.80 | 547.84 | 41.4 | 19.83 | 473.26 | 32.2 | 13.32 | 420.11 | 23.6 | 8.67 |
| 28 | 694.76 | 53.8 | 30.37 | 574.86 | 44.2 | 20.63 | 496.56 | 35.4 | 14.27 | 440.76 | 27.2 | 9.74 |
| 29 | 727.86 | 55.9 | 30.82 | 602.20 | 46.7 | 21.39 | 520.14 | 38.3 | 15.09 | 461.65 | 30.5 | 10.66 |
| 30 | 761.34 | 57.9 | 31.16 | 629.85 | 49.1 | 21.86 | 543.98 | 41.0 | 15.79 | 482.77 | 33.6 | 11.46 |
| 31 | 795.19 | 59.7 | 31.43 | 657.82 | 51.2 | 22.33 | 568.09 | 43.5 | 16.38 | 504.14 | 36.4 | 12.15 |
| 32 | 829.41 | 61.3 | 31.62 | 686.08 | 53.2 | 22.71 | 592.46 | 45.9 | 16.89 | 525.73 | 39.0 | 12.74 |
| 33 | 863.99 | 62.9 | 31.76 | 714.63 | 55.1 | 23.03 | 617.08 | 48.0 | 17.32 | 547.54 | 41.4 | 13.26 |
| 34 | 898.91 | 64.3 | 31.84 | 743.48 | 56.9 | 23.28 | 641.95 | 50.0 | 17.69 | 569.58 | 43.7 | 13.70 |
| 35 | 934.18 | 65.7 | 31.88 | 772.60 | 58.5 | 23.48 | 667.06 | 51.9 | 18.00 | 591.83 | 45.8 | 14.09 |
| 36 | 969.78 | 66.9 | 31.88 | 802.01 | 60.0 | 23.64 | 692.42 | 53.7 | 18.26 | 614.29 | 47.8 | 14.42 |
| 37 | 1005.72 | 68.1 | 31.85 | 831.68 | 61.4 | 23.76 | 718.00 | 55.3 | 18.47 | 636.95 | 49.6 | 14.70 |
| 38 | 1041.97 | 69.2 | 31.80 | 861.63 | 62.8 | 23.85 | 743.82 | 56.9 | 18.65 | 659.83 | 51.4 | 14.95 |
| 39 | 1078.55 | 70.3 | 31.72 | 891.83 | 64.0 | 23.90 | 769.86 | 58.3 | 18.80 | 682.90 | 53.0 | 15.16 |
| 40 | 1115.44 | 71.2 | 31.62 | 922.30 | 65.3 | 23.93 | 796.12 | 59.7 | 18.91 | 706.17 | 54.6 | 15.33 |
| 41 | 1152.63 | 72.2 | 31.50 | 953.01 | 66.3 | 23.94 | 822.60 | 61.0 | 19.01 | 729.63 | 56.0 | 15.48 |
| 42 | 1190.13 | 73.0 | 31.38 | 983.98 | 67.4 | 23.94 | 849.30 | 62.2 | 19.07 | 753.28 | 57.4 | 15.61 |
| 43 | 1227.93 | 73.9 | 31.23 | 1015.19 | 68.4 | 23.91 | 876.21 | 63.4 | 19.12 | 777.12 | 58.7 | 15.71 |
| 44 | 1266.02 | 74.7 | 31.08 | 1046.63 | 69.4 | 23.87 | 903.33 | 64.5 | 19.16 | 801.14 | 60.0 | 15.80 |
| 45 | 1304.40 | 75.4 | 30.92 | 1078.34 | 70.3 | 23.82 | 930.65 | 65.5 | 19.17 | 825.34 | 61.1 | 15.86 |
| 46 | 1343.06 | 76.1 | 30.76 | 1110.27 | 71.2 | 23.75 | 958.17 | 66.5 | 19.18 | 849.72 | 62.2 | 15.91 |
| 47 | 1382.00 | 76.8 | 30.58 | 1142.42 | 71.9 | 23.68 | 985.90 | 67.5 | 19.17 | 874.28 | 63.3 | 15.95 |
| 48 | 1421.22 | 77.4 | 30.41 | 1174.81 | 72.7 | 23.60 | 1013.81 | 68.4 | 19.15 | 899.02 | 64.3 | 15.98 |
| 49 | 1460.71 | 78.0 | 30.23 | 1207.42 | 73.4 | 23.51 | 1041.93 | 69.2 | 19.12 | 923.92 | 65.3 | 15.99 |
| 50 | 1500.47 | 78.6 | 30.04 | 1240.25 | 74.1 | 23.41 | 1070.23 | 70.0 | 19.09 | 948.99 | 66.2 | 15.99 |
| 51 | 1540.50 | 79.2 | 29.85 | 1273.30 | 74.8 | 23.31 | 1098.72 | 70.8 | 19.04 | 974.23 | 67.1 | 16.00 |
| 52 | 1580.78 | 79.7 | 29.67 | 1306.57 | 75.4 | 23.21 | 1127.40 | 71.5 | 18.99 | 999.64 | 67.9 | 15.98 |
| 53 | 1621.33 | 80.2 | 29.48 | 1340.06 | 76.1 | 23.10 | 1156.26 | 72.3 | 18.94 | 1025.20 | 68.7 | 15.97 |
| 54 | 1662.13 | 80.7 | 29.29 | 1373.74 | 76.6 | 22.99 | 1185.30 | 72.9 | 18.87 | 1050.93 | 69.5 | 15.94 |
| 55 | 1703.18 | 81.2 | 29.09 | 1407.64 | 77.2 | 22.87 | 1214.53 | 73.6 | 18.81 | 1076.81 | 70.2 | 15.91 |
| 56 | 1744.48 | 81.6 | 28.90 | 1441.74 | 77.8 | 22.76 | 1243.92 | 74.2 | 18.74 | 1102.86 | 70.9 | 15.88 |
| 57 | 1786.03 | 82.0 | 28.71 | 1476.05 | 78.3 | 22.64 | 1273.50 | 74.8 | 18.67 | 1129.05 | 71.6 | 15.84 |
| 58 | 1827.82 | 82.5 | 28.52 | 1510.56 | 78.8 | 22.52 | 1303.24 | 75.4 | 18.59 | 1155.40 | 72.2 | 15.80 |
| 59 | 1869.85 | 82.8 | 28.33 | 1545.26 | 79.2 | 22.39 | 1333.16 | 75.9 | 18.52 | 1181.90 | 72.9 | 15.75 |
| 60 | 1912.12 | 83.2 | 28.14 | 1580.16 | 79.7 | 22.27 | 1363.25 | 76.5 | 18.44 | 1208.55 | 73.5 | 15.70 |

BASELINE CONTACT AREA
MINIMUM % AREA OF RELIEF (COMPARED WITH UNINTERRUPTED BEARING SURFACE)
MINIMUM % AREA OF RELIEF (COMPARED WITH TOTAL ARTICULAR SURFACE)
MAXIMUM % AREA OF RELIEF (COMPARED WITH UNINTERRUPTED BEARING SURFACE)
MAXIMUM % AREA OF RELIEF (COMPARED WITH TOTAL ARTICULAR SURFACE)

PROSTHETIC JOINTS HAVING REDUCED AREA BEARING SURFACES AND APPLICATION THEREOF TO A RANGE OF SIZES OF PROSTHETIC JOINTS

This application is a continuation of application Ser. No. 10/025,945, filed on Dec. 19, 2001 now U.S. Pat. No. 6,660,040. The disclosure of the above-identified patent application is hereby totally incorporated by reference in its entirety.

BACKGROUND

1. Field of the Invention

The present invention relates to prosthetic devices used for replacement of a natural joint and, more particularly, to prosthetic joints having reduced area bearing surfaces.

2. Background Information

It is known to provide prosthetic joints or joint assemblies for acetabulums, knees, ankles, shoulders, elbows, and wrists. Components of prosthetic joints such as that shown in U.S. Pat. No. 4,068,342 to Townley et al., provide a face having a continuous surface area of articulation for its corresponding member. While conventional prosthetic components beneficially provide a low-friction articular face for the surface of accompanying member, interaction between the articulating component and the member can produce joint debris. Such debris is expelled into the adjacent tissues and may cause adverse reactions in the surrounding bodily tissue.

Attempts have been made to prevent joint debris produced by prosthesis joint assemblies from entering surrounding bodily tissue. See for example, U.S. Pat. No. 4,731,088 to Collier, where a flexible enclosure is applied to a prosthetic joint to isolate the joint debris from the surrounding tissue. It is thus desirable to reduce wear associated with prosthesis joint assemblies.

Prosthesis joint assemblies may be fabricated from various materials. There are hard on hard bearing prosthetic joint assemblies and polyethylene on hard bearing prosthetic joint assemblies. Hard on hard bearing prosthetic joint assemblies or combinations are typically metal-metal or ceramic-ceramic. Polyethylene on hard bearing prosthetic joint assemblies or combinations are typically polyethylene-metal.

For hard-on-hard bearing combinations of an acetabular cup assembly, for example, a lower head to cup clearance (gap) results in lower wear. As well, smaller diameter implants have been associated with lower friction. As implant diameter (head and inner cup with respect to an acetabular cup assembly) increases, the same low clearance for a smaller diameter bearing combination results in a higher contact area for the larger bearing combinations. This results in a higher frictional torque and a reduction in the size of an inlet zone. Excessive reduction in the size of the inlet zone may reduce the potential for lubrication to occur. For polyethylene-on-hard bearing combinations, which have typically been smaller diameter implants, implant wear increases with implant diameter and decreasing clearance. The current trend, however, is towards larger diameter implants.

In view of the above and other considerations, it is an object of the subject invention to provide an improved prosthetic joint.

It is another object of the subject invention to provide an improved joint prosthesis having a surface that minimizes the production of joint debris which can result from articulating movement of the joint prosthesis post implantation.

Another object of the subject invention is to provide an improved prosthetic component of a joint prosthesis having a bearing surface that minimizes the production of joint debris which can result from articulating movement of the prosthetic component post implantation.

Still another object of the subject invention is to provide an improved prosthetic joint that has surfaces that maximizes lubricity in conjunction with a corresponding prosthetic component when implanted in a patient.

A further object of the subject invention is to provide a method of fabricating a prosthetic assembly that has an optimum contact or bearing area.

A still further object of the subject invention is to provide a method of fabricating a prosthetic assembly that has an optimum contact area for a range of prosthetic assembly sizes.

SUMMARY

The subject invention is a prosthetic joint having a reduced area bearing surface, a method of determining the reduced area bearing surface for the prosthetic joint, and application of the determination of the reduced area bearing surface to a range of sizes of like prosthetic joints. Particularly, the subject invention is a prosthetic joint having interruptions in the bearing surface thereof that define the reduced area bearing surface, a method of determining an amount of interruptions (or of an amount of remaining bearing surface area) for the prosthetic joint, and the application thereof to a range of sizes of like prosthetic joints.

For hard-on-hard prosthetic bearing combinations and polyethylene-on-hard prosthetic bearing combinations, optimally designed interruptions in an articular face of one or both of the prosthetic bearing components provides a specific contact area or bearing surface that may be deemed "optimum." This is achieved for a wide range of sizes of the particular prosthetic and/or prosthetic bearing component, while still maintaining the same low bearing component-to-bearing component clearance of the prosthetic assembly.

Optimally decreasing contact area in the articulating surface of one or both bearing components of the prosthetic assembly through interruptions in the surface thereof, provides benefits of larger diameter prosthetic components (with an associated increased range of motion, and decreased potential for dislocation), low frictional torques, and lower wear of smaller diameter prosthetic components.

In one form, the subject invention provides a bearing component for a prosthetic assembly. The bearing component includes a body having an articular surface. The articular surface has areas of relief that define an interrupted bearing surface. The areas of relief range from 0.3% to 83.2% relative to an otherwise uninterrupted bearing surface area, and from 0.01% to 31.88% relative to a total articular surface area.

In another form, the subject invention provides a bearing component for a prosthetic assembly. The bearing component includes a body defining an articular surface area. The articular surface area has a contact surface area defined by interruptions, wherein the interruptions range from 0.3% to 83.2% relative to an otherwise uninterrupted contact surface area, and from 0.01% to 31.88% relative to the articular surface area.

In another form, the subject invention provides a prosthetic joint assembly. The prosthetic joint assembly includes a first bearing component and a second bearing component. The first bearing component has an articular surface area adapted to receive the second bearing component. The articular surface area has a bearing surface area that is defined by interruptions, and is adapted to be contacted by the second bearing component. The interruptions range from 0.3% to 83.2% relative to an otherwise uninterrupted bearing surface area, and from 0.01% to 31.88% relative to the articular surface area.

In yet another form, the subject invention provides a method of making a bearing component for a prosthetic assembly. The method includes steps of: (a) forming a body having an articular surface; and (b) forming areas of relief in the articular surface to define an interrupted bearing surface wherein the areas of relief range from 0.3% to 83.2% relative to an otherwise uninterrupted bearing surface, and from 0.01% to 31.88% relative to a total articular surface area.

In still another form, the subject invention provides a method of making a bearing component for a prosthetic assembly. The method includes the steps of: (a) forming a body defining an articular surface area; and (b) forming the articular surface area with a contact surface area defined by interruptions wherein the interruptions range from 0.3% to 83.2% relative to an otherwise uninterrupted contact surface area, and from 0.01% to 31.88% relative to the articular surface area.

In a yet further form, the subject invention provides a method of making a prosthetic joint having a first body and a second body. The method includes the steps of: (a) determining a clearance distance between the first body and the second body; (b) determining a contact surface area value for the first and second body based on the clearance distance; and (c) forming the first body with interruptions in an articular surface thereof such that a bearing surface area defined by the interruptions in the articular surface equals the contact surface area value.

In another form, the subject invention provides a method of making a prosthetic assembly comprising a first body of a first material and a second body of a second material. The method includes the steps of: (a) determining a clearance distance between the first and second body; (b) deriving a baseline contact area value for the prosthetic assembly; and (c) providing interruptions in an articular surface of one of the first and second bodies based on the baseline contact area value, the interruptions providing an optimum contact area between the first and second bodies that is constant for a range of prosthetic assembly sizes.

The interruptions may be formed in only one prosthetic component or both prosthetic components (e.g. head and liner) of the prosthetic assembly/joint. Further, the interruptions may be formed macroscopically and/or microscopically.

BRIEF DESCRIPTION OF THE DRAWINGS

The detailed description particularly refers to the accompanying figures in which:

FIG. 9 is a cross-sectional view similar to FIG. 2 of another exemplary embodiment of a bearing component according to the principles of the subject invention showing the interrupted articular face having a generally hemispherical bearing surface and a plurality of very fine to extremely fine intersecting grooves or channels extending into the surface;

FIG. 10 is a cross-sectional view similar to FIG. 2 of another exemplary embodiment of a bearing component according to the principles of the subject invention showing the interrupted articular face having a generally hemispherical bearing surface and a plurality of very fine to extremely fine grooves or channels extending into the surface;

FIG. 14 is a perspective view of another exemplary embodiment in accordance with the principles of the subject invention showing a prosthetic bearing component for an extreme distal end of a femur, and the bearing component having interrupted condyles;

FIG. 15 is a perspective view of yet another exemplary embodiment according to the principles of the subject invention showing a prosthetic bearing component for an extreme proximal end of the tibia and the bearing component showing two slightly concave interrupted bearing surfaces corresponding to the medial and labial condyles of the tibia;

FIG. 18 is a table showing a baseline contact area and calculated percentage areas of relief relative to both an uninterrupted contact area and a total articular surface area for metal on metal bearing components of various sizes in accordance with the principles of the subject invention;

FIG. 20 is a table showing a baseline contact area and calculated percentage areas of relief relative to both an uninterrupted contact area and a total articular surface area for ceramic on ceramic bearing components of various sizes in accordance with the principles of the subject invention;

FIG. 22 is a table showing a baseline contact area and calculated percentage areas of relief relative to both an uninterrupted contact area and a total articular surface area for metal on plastic (polyethylene) bearing components of various sizes in accordance with the principles of the subject invention.

Corresponding reference characters indicate corresponding parts throughout the several views.

DETAILED DESCRIPTION

The subject invention is based upon a hypothesis and resulting principles that a prosthetic assembly having a bearing component with an articular face, interrupted by either recesses or protrusions, minimizes production of joint debris created by the interaction between the articular face and an accompanying joint face articulation component. This decrease is believed to be the result of the reduction in available surface area of articulation between the components, in comparison with traditional bearing components having smooth uninterrupted articulation faces. In accordance with the principles of the subject invention, one or both bearing components allow utilization of, for example, a large ball diameter for enhancement of joint stability while increasing lubrication and minimizing the production of undesirable joint debris.

It has been found that it is possible to provide intentional interruptions in the articular face of a prosthetic component through the application of lubrication and contact mechanics theory to yield a prosthetic component that has an optimum contact area, particularly with regard to wear and lubrication. More particularly, it has been found that such optimization of interruptions in the articular face of one or both prosthetic components of a prosthetic assembly, extends to a wide range of sizes of the prosthetic component. Such extension is constant for a wide range of sizes of a particular prosthetic component such as diameters of a head and inner cup of a prosthetic acetabular cup assembly. It should be appreciated that while the subject invention specifically applies to ball and socket or joint type prosthetic assemblies, the present hypothesis and/or principles may apply equally to other types of prosthetic assemblies.

Figure 1:
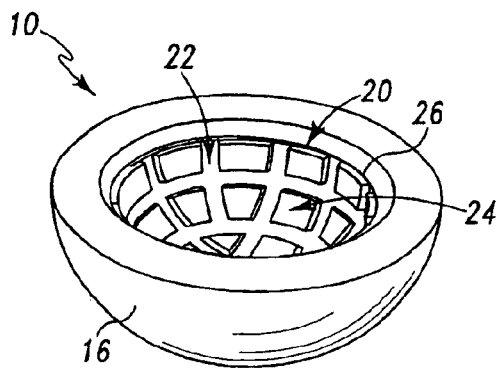
FIG. 1 is a perspective view of an exemplary embodiment of a bearing component of a prosthesis in accordance with the principles of the subject invention and showing an exterior and an opposite internal cavity defined by an interrupted articular face suitable for engaging a ball.

Referring now to FIG. 1, an exemplary bearing component 10 for a prosthesis (prosthetic joint) is shown having an exterior suitable for engagement with the acetabulum or use with a support cup (not shown). Acetabular cups are mounted in the acetabulum using a variety of techniques, of which all are well known in the orthopaedic field. While the exemplary bearing component 10 has an outer surface 16 that is generally hemispherical in shape to be received in a typical acetabular cup or shell, it is contemplated that it may take on a variety of forms in order to cooperate with either the acetabulum or with the acetabular support cup. For an example of a technique for mounting the bearing 10 in a support cup, see U.S. Pat. No. 5,049,158 to Engelhardt et al., the relative portions of which are specifically incorporated herein by reference. The bearing component 10 may be mounted within the support cup, or even in the acetabulum, using a variety of known attachment methods. See for example U.S. Pat. No. 4,9004,265 to MacCollum et al. and U.S. Pat. No. 5,002,577 to Bolesky et al.

The bearing component 10 illustratively comprises an interior 20 that forms an internal cavity 22 suitable for receiving a femoral head (not shown) therein and a preferably one-piece interrupted articular face or surface 24 for engagement and articulation with the femoral head. The term "one-piece" is used herein to mean that the articular face is itself shaped, molded, or formed to include the interruptions. The interrupted articular face 24 of the bearing component 10 minimizes, optimizes, and/or adjusts the available surface area of articulation with the femoral head. Illustratively, the interior 20 of the bearing component 10 includes a mouth 26 extending about the internal cavity 22 and the circumference of the face 24. The mouth 26 of the bearing component 10 defines a plane through which the femoral head enters the interior 20 of the bearing component 10 for engagement and articulation with the interrupted articular face 24.

The embodiments of one type of bearing component formed in accordance with the principles of the subject invention that are illustrated in FIGS. 1–8 are formed for use with an acetabular prosthetic joint. However, as will be subsequently discussed, it is contemplated that various patterns of interruptions within the articular face 24 (and/or the articular faces of the other embodiments shown and/or described herein) may also be incorporated into other prosthetic joints not specifically shown and/or described herein. Thus, the present principles may be applied to a glenoid, patellar, femoral, humoral, tibial, ulnar, radial, wrist, and/or ankle component for a corresponding prosthetic joint assembly. Further, it is contemplated that the various patterns of interruptions within the articular face 24 (and/or the articular faces of the other embodiment shown and/or described herein) may be modified in accordance with the principles of the subject invention to yield patterns not specifically shown or described herein.

It is understood that the bearing component in accordance with the subject invention can be made from any material that is biocompatible and that will undergo articulating movement with a corresponding natural or prosthetic member. For example, the bearing component could be formed from a variety of metals, plastics, ceramics, or composite materials. In the event that plastics are chosen, a high density polyethylene and, more particularly an ultra-high molecular weight polyethylene (UHMWPE), may be used, although numerous types of plastics may be suitable for purposes of the invention so long as the material provides both strength and a low-friction articulation surface for the corresponding joint face. Further, the bearing component is accordance with the subject invention is constructed in accordance with well-known methods of manufacture. For example, it is understood that a metal shell can be cast, forged, or machined to include the interrupted articular face while ceramic, plastic, and composite materials suggest other well-known methods of manufacture.

In one embodiment of the bearing component, the interrupted articular face 24 of the interior 20 includes a smooth spherically concave, generally hemispherical bearing surface 30 and a plurality of recesses 32 formed within the surface 30. The recesses 32 cause the bearing surface 30 to be interrupted, and thus divided into individual bearing surfaces. The total bearing surface area for the bearing component 10 thus consists of the total of the area of each individual bearing platform 31. The area of the recesses 32 makes up a total recessed area for the bearing component 10. The total recess area plus the total bearing surface area equals the total articular face 24 area for the bearing component 10. The total area of the recesses or, alternatively, the total area of the bearing surface is optimized and/or adjusted for low wear and high lubricity for the bearing component 10. Such optimization/adjustment may then be transferred to a same type of bearing component but of a different size.

Particularly, and as explained in detail hereinbelow in accordance with the principles of the subject invention, the percentage of interruptions or reliefs relative to the percentage of bearing surface area, platform surface area, or the total articular face or surface area is calculated in accordance with lubrication and contact mechanics theory. More particularly, the percentage of area formed by interruptions or reliefs or, alternatively, the percentage of area formed by the platforms, lands, or bearing surfaces, is optimized/ adjusted in accordance with lubrication and contact mechanics theory to provide appropriate clearance and maximum lubrication for a bearing component. The appropriate clearance depends on the type of material(s) used for the prosthetic joint. Particularly, clearance is minimum for metal to metal and ceramic to ceramic components, but larger for metal to polyethylene components. It should also be understood and appreciated that the recesses may be formed and positioned in a variety of manners so long as the surface area of articulation is reduced from that of an uninterrupted smooth articular face (not shown) for an equivalently sized bearing component. As such, it should be appreciated that the interruptions may be formed on a macroscopic basis, as shown, or on a microscopic basis. Regarding the microscopic basis, the interruptions may be formed on an order of less than one millimeter (1 mm), such as on a micrometer or nanometer scale.

Figure 2:
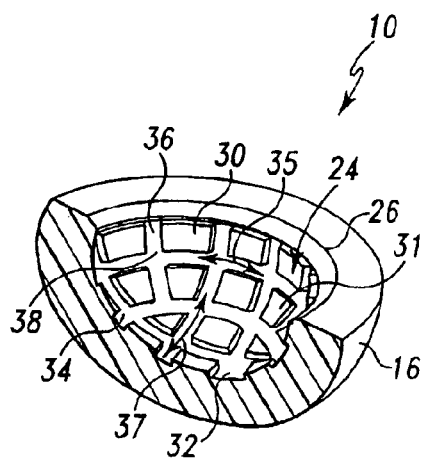
FIG. 2 is a cross-sectional view of the bearing component of FIG. 1 showing an interior of the bearing component including a mouth that defines the internal cavity and the interrupted articular face of the internal cavity having a generally hemispherical bearing surface and a plurality of intersecting grooves or channels extending into the surface.

As best shown in FIG. 2, the recesses 32 may be formed as grooves 34 and 36. Illustratively, the bearing surface 30 is defined by a plurality of bearing platforms or lands 31 integral with the face 24 and grooves or channels 34 extending about the bearing surface 30 and between the platforms 31 substantially parallel as shown by the arrow 35 to the mouth 26. Additionally, the interrupted articular face 24 includes grooves or channels 36 extending between the platforms 31 substantially perpendicular, as shown the by arrow 37, relative to the mouth 26. Thus the grooves 34 and 36 illustratively cross one another at intersections 38. Grooves 34 and 36 are positioned in spaced-apart relation to one another about the bearing surface 30 of the interrupted articular face 24. However, it is contemplated that the grooves 34 and 36 may vary in number and positioning about the surface 30 of the interrupted articular face 24.

Figure 3:
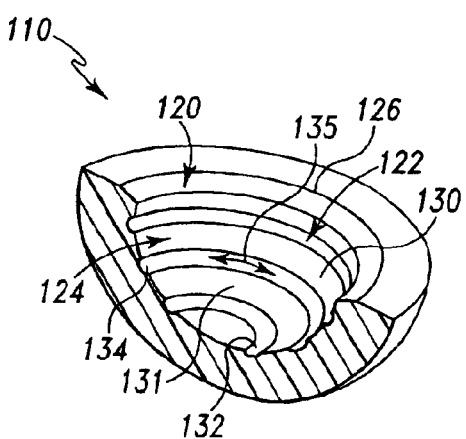
FIG. 3 is a cross-sectional view similar to FIG. 2 of another exemplary embodiment of a bearing component according to the principles of the subject invention showing the interrupted articular face having a generally hemispherical bearing surface and a plurality of grooves or channels extending into the surface substantially parallel to the mouth.

Another embodiment of the bearing component is illustrated in FIG. 3. The bearing component 110 includes an interior 120 forming an internal cavity 122 and a mouth 126 extending about the cavity 122. Further, the interior 120 includes a preferably one-piece interrupted articular face 124. The interrupted articular face 124 has a bearing surface 130 defined by a plurality of bearing platforms or lands 131 integral with the articular face 124 and a plurality of recesses 132 that extend into the surface 130. The recesses 132 are formed as grooves or channels 134 extending about the bearing surface 130 between the platforms 131 substantially parallel, as shown by the arrow 135 to the mouth 126. Illustratively, the grooves 134 are positioned in spaced-apart relation to one another about the bearing surface 130 of the articular face 124.

Figure 4:
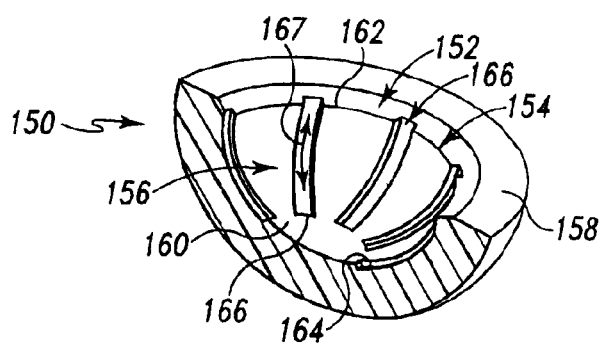
FIG. 4 is a cross-sectional view similar to FIG. 2 of another exemplary embodiment of a bearing component according to the principles of the subject invention showing the interrupted articular face having a generally hemispherical bearing surface and a plurality of grooves or channels extending into the surface substantially perpendicular to the mouth.

Yet another embodiment of the subject invention is illustrated in FIG. 4. A bearing component 150 includes an interior 152 that forms an internal cavity 154 and a one-piece interrupted articular face 156. Additionally, the interior 152 includes a mouth 158 extending about the cavity 154. The interrupted articular face 156 of the interior 152 includes a generally hemispherical bearing surface 160 defined by a plurality of bearing platforms 162 integral with the face 156 and recesses 164 formed as grooves or channels 166 extending about the surface 160 between platforms or lands 162 and substantially perpendicular, as shown by the arrow 167 to the mouth 158. Moreover, the grooves 166 are illustratively positioned in spaced-apart relation to one another about the bearing surface 160 of the articular face 156.

Figure 5:
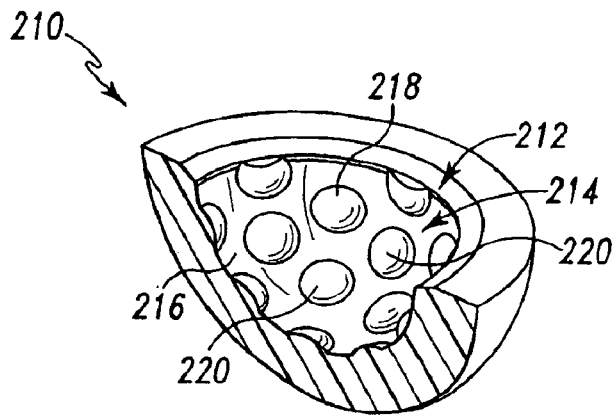
FIG. 5 is a cross-sectional view similar to FIG. 2 of another exemplary embodiment of a bearing component according to the principles of the subject invention showing the interrupted articular face having a generally hemispherical bearing surface and a plurality of bearing platforms integral with the articular face and protruding into the internal cavity.

In another embodiment of the subject invention, shown in FIG. 5, a bearing component 210 includes an interior 212 that forms an internal cavity 214 and a one-piece interrupted articular face 216. Illustratively, the articular face 216 is formed to include a generally hemispherical bearing surface 218 defined by a plurality of bearing platforms or lands 220 integral with the articular face 216 and protruding into the cavity 214. Thus, the femoral head (not shown) will engage and articulate upon the platforms 220 of the interrupted articular face 216 upon insertion into the cavity 214 of the bearing component 210. Illustratively, the platforms 220 are positioned in spaced-apart relation to one another about the interrupted articular face 216. It is understood that while the platforms 220, as shown in FIG. 5, are generally convex in shape, they may take on a number of forms so long as a low friction articular face 216 is provided for the femoral head.

Figure 6:
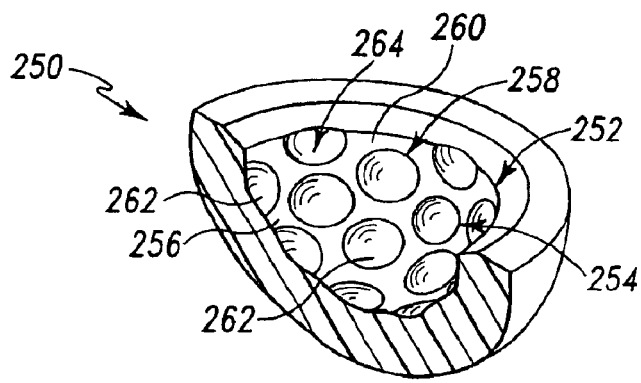
FIG. 6 is a cross-sectional view similar to FIG. 2 of another exemplary embodiment of a bearing component according to the principles of the subject invention showing the interrupted articular face having a generally hemispherical bearing surface and a plurality of concave dimples extending into the bearing surface.

Further, another embodiment of the subject invention is illustrated in FIG. 6. A bearing component 250 includes an interior 252 having an internal cavity 254 and a one-piece interrupted articular face 256. The interrupted articular face 256 includes a smooth generally hemispherical bearing surface 260 defined by a plurality of bearing platforms or lands 258 integral with the articular face 256. Moreover, generally concave dimples 262 extend into the articular face 256 between the platforms 258 to interrupt the surface 260. The dimples 262 define a plurality of recesses 264 formed into the surface 260 of the interrupted articular face 256. Moreover, the dimples 262 are illustratively positioned in spaced-apart relation to one another about the bearing surface 260 of the interrupted articular face 256.

Figure 7:
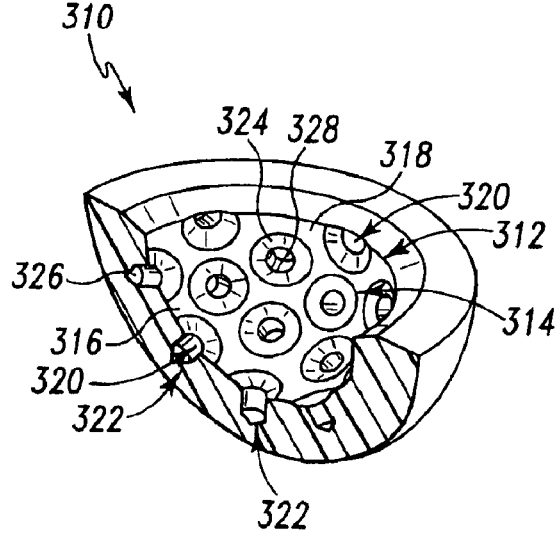
FIG. 7 is a cross-sectional view similar to FIG. 2 of another exemplary embodiment of a bearing component according to the principles of the subject invention showing the interrupted articular face having a generally hemispherical bearing surface and a plurality of sockets extending into the bearing surface.

Another embodiment of the subject invention is illustrated in FIG. 7. The bearing component 310 includes an interior 312 having an internal cavity 314 and a one-piece interrupted articular face 316. The articular face 316 includes a smooth generally hemispherical bearing surface 318 and a plurality of sockets 320 defining recesses 322 extending into the surface 318. Each socket 320 includes a conical-shaped mouth 324, a conical-shaped base 326, and a cylindrical sidewall 328 extending between the mouth 324 and the base 326. Illustratively, the sockets 322 are positioned in spaced-apart relation to one another about the bearing surface 318 of the articular face 316. However, it is contemplated that the number and positioning of the sockets 322 may be varied.

Figure 8:
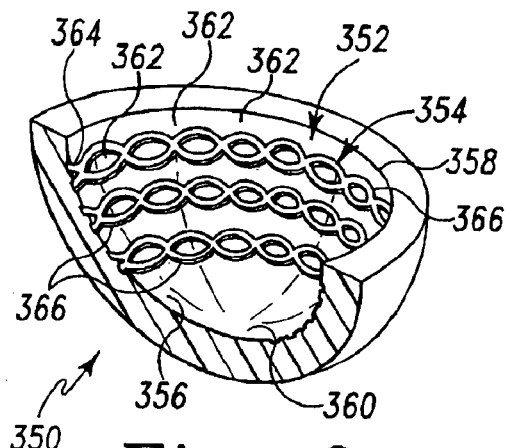
FIG. 8 is a cross-sectional view similar to FIG. 2 of another exemplary embodiment of a bearing component according to the principles of the subject invention showing the interrupted articular face having a generally hemispherical bearing surface and a plurality of grooves or channels extending into the surface and randomly weaving thereabout.

Another bearing component in accordance with the principles of the subject invention is illustrated in FIG. 8. The bearing component 350 illustratively comprises an interior 352 that forms an internal cavity 354 suitable for receiving a femoral head (not shown) therein and a one-piece interrupted articular face 356 for engagement and articulation with the femoral head. The interrupted articular face 356 of the bearing component 350 minimizes available surface area of articulation with the femoral head, as does all of the illustrated bearing components with respect to a corresponding bearing component.

Illustratively, the interior 352 of the bearing component 350 includes a mouth 358 extending about the circumference of the internal cavity 354. The mouth 358 of the bearing component 350 defines a plane through which the femoral head enters the interior 352 of the bearing component 350 for engagement and articulation with the interrupted articular face 356. The interrupted articular face 356 of the interior 352 includes a smooth generally hemispherical bearing surface 360 defined by a plurality of bearing platforms or lands 362 and a plurality of recesses 364 formed therein between the platforms 362. The bearing surface 360 is integral with the articular face 356 while the grooves 366 weave about the bearing surface 360 and between the platforms 362.

Another bearing component in accordance with the principles of the subject invention is illustrated in FIG. 9. The bearing component 600 illustratively comprises an interior 602 that forms an internal cavity 604 suitable for receiving a femoral head (not shown) therein and a one-piece interrupted articular face 606 for engagement and articulation with the femoral head. The interrupted articular face 606 of the bearing component 600 minimizes available surface area of articulation with the femoral head, as does all of the illustrated bearing components with respect to a corresponding bearing component.

Illustratively, the interior 602 of the bearing component 600 includes a mouth 608 extending about the circumference of the internal cavity 604. The mouth 608 of the bearing component 600 defines a plane through which the femoral head enters the interior 602 of the bearing component 600 for engagement and articulation with the interrupted articular face 606. The interrupted articular face 606 of the interior 602 includes a smooth generally hemispherical bearing surface 610 defined by a plurality of micro bearing platforms or lands 612 and a plurality of micro recesses 614 formed therein between the micro platforms 612. The bearing surface 610 is integral with the articular face 606 while the micro grooves 614 run horizontally and vertically about the bearing surface 610 and between the micro platforms 612. It should be appreciated that the bearing component 600 is exemplary of interruptions formed on a microscopic scale. The exact depiction of microscopic interruptions on the order of less than one millimeter, and preferably on the order of micrometers to nanometers, is intended to be encompassed by the illustrative embodiment of FIG. 9. This includes micro-dimples and other micro structures. As well, it should be appreciated that the subject invention may be embodied as surface positive and/or surface negative features, particularly the interruptions and/or bearing surface thereof.

Another bearing component in accordance with the principles of the subject invention is illustrated in FIG. 10. The bearing component 650 illustratively comprises an interior 652 that forms an internal cavity 654 suitable for receiving a femoral head (not shown) therein and a one-piece interrupted articular face 656 for engagement and articulation with the femoral head. The interrupted articular face 656 of the bearing component 650 minimizes available surface area of articulation with the femoral head, as does all of the illustrated bearing components with respect to a corresponding bearing component.

Illustratively, the interior 652 of the bearing component 650 includes a mouth 658 extending about the circumference of the internal cavity 654. The mouth 658 of the bearing component 650 defines a plane through which the femoral head enters the interior 652 of the bearing component 650 for engagement and articulation with the interrupted articular face 656. The interrupted articular face 656 of the interior 652 includes a smooth generally hemispherical bearing surface 660 defined by a plurality of generally annular micro bearing platforms or lands 662 and a plurality of generally annular micro recesses 664 formed therein between the micro platforms 662. The bearing surface 660 is integral with the articular face 656 while the micro grooves 664 run annularly about the bearing surface 660 and between the annularly running micro platforms 662. It should be appreciated that the bearing component 650 is exemplary of interruptions formed on a microscopic scale. The exact depiction of microscopic interruptions on the order of less than one millimeter, and preferably on the order of micrometers to nanometers, is intended to be encompassed by the illustrative embodiment of FIG. 10.

From the foregoing, it should be appreciated that the various patterns of platforms and/or interruptions shown formed in the articular faces of the various bearing components (either only one bearing component of the prosthesis assembly/joint, or both bearing components of the prosthesis assembly/joint) may be formed in either the macroscopic realm, the microscopic realm, or a combination of macroscopic and microscopic realms.

Figure 11:
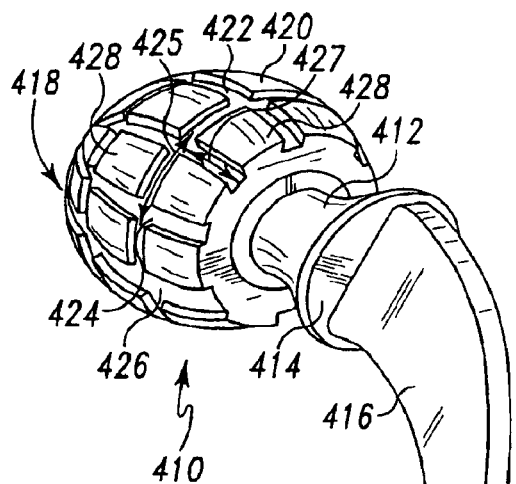
FIG. 11 is a perspective view of another exemplary embodiment of a bearing component in accordance with the principles of the subject invention showing a ball attached to a stem for a hip, the ball including an interrupted articular face having a bearing surface and a plurality of intersecting grooves or channels extending into the surface.

Another bearing component is accordance with the principles of the subject invention is illustrated in FIG. 11. A ball head bearing component 410 is provided for attachment to a neck 412. The neck 412 is connected to a platform 414 that is then connected to an arcuate stem or shaft 416. The ball head component 410 is insertable into the acetabular socket of the pelvis (not shown) once the prosthesis has been securely anchored in the femur. The ball head component 410 may work equally well with a natural acetabular socket or with any variety of artificial acetabular cups. As with all of the other embodiments of the subject invention, the dimensions of the ball head 410 can be easily varied to adapt to the particular bone structure of the patient or to the dimensions of the corresponding implanted prosthetic component. In accordance with the principles of the subject invention, the percentage area of the interruptions and/or platforms relative to each other, or to the total articular surface area, is constant regardless of prosthesis size. While a ball head component 410 is illustratively used as a hip joint prosthesis, it is contemplated that the ball head component, in accordance with an aspect of the subject invention, could also be formed as a humeral head (not shown) for a shoulder joint prosthesis. For further description of a ball head see U.S. Pat. No. 4,068,216 to Townley et al., the relevant portions of which are specifically incorporated herein by reference.

The ball head component 410 comprises a one-piece interrupted articular socket-engaging face 418 that reduces surface area of articulation between the ball 410 and the corresponding socket (not shown). The interrupted articular socket-engaging face 418 of the ball head component 410 includes a smooth spherically convex, generally hemispherical bearing surface 420 and a plurality of recesses 422 formed with the surface 420. Illustratively, the recesses 422 are formed as grooves or channels 424 and 426. The bearing surface 420 is defined by a plurality of bearing platforms or lands 428 integral with the face 418 and the grooves 424 and 426 extend between the platforms 428. Preferably, the grooves 424 extend in the direction shown by the arrow 425 while the grooves 426 extend in the direction shown by the arrow 427 between the platforms 428. It is understood that the grooves 424 and 426 may extend about the bearing surface 420 in a variety of manners, so long as the surface area of articulation between the ball 410 and the corresponding socket is reduced.

Figure 12:
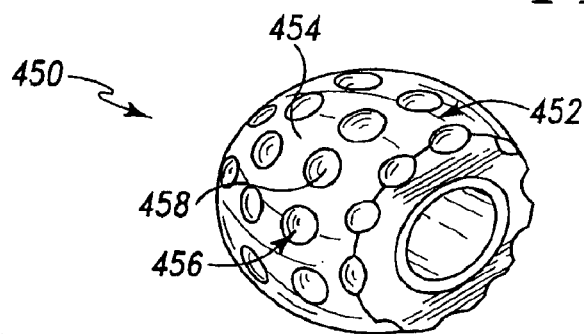
FIG. 12 is a perspective view of an exemplary bearing component in accordance with the present invention showing a ball having an interrupted articular face having a plurality of concave dimples extending into the surface.

Another embodiment of the bearing component in accordance with the principles of the subject invention is illustrated in FIG. 12. A ball head component 450 includes a preferably one-piece interrupted articular socket-engaging face 452 that reduces surface area of articulation between the ball 450 and the corresponding socket (not shown). The interrupted articular socket-engaging face 452 of the ball head component 450 includes a smooth generally spherical bearing surface 454 and a plurality of recesses 456 that are formed as generally concave dimples 458. The dimples 458 extend into the surface 454. Illustratively, the recesses 456 are formed similarly to the dimples 262 shown in FIG. 6.

Figure 13:
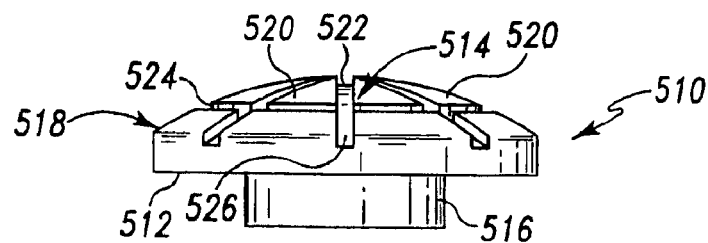
FIG. 13 shows an elevational view of another exemplary embodiment of a bearing component in accordance with the principles of the subject invention showing a patellar implant having an articular face interrupted by a plurality of bearing platforms with grooves or channels extending therebetween.

Another embodiment of the bearing component in accordance with the principles of the subject invention is illustrated in FIG. 13. A patellar joint bearing component 510 comprises a bone facing surface 512 and a preferably one-piece interrupted articular facing surface 514 opposite the bone facing surface 512. Additionally, a protuberance 516 extends from the bone facing surface 512. For further description of a patellar joint implant see U.S. Pat. No. 4,964,867 to Boger, the relevant portions of which are specifically incorporated herein by reference. The interrupted articular surface 514 of the patellar joint implant 510 minimizes available surface area of articulation with the femoral component of the knee (not shown). The interrupted articular face 514 includes a smooth generally convex bearing surface 518 defined by a plurality of bearing platforms or lands 520 integral with the face 514 and a plurality of recesses 522 formed within the surface 518. Illustratively, the recesses 522 are formed as grooves or channels 524 and 526 that extend between the platforms 520. It is understood that the surface 514 may be interrupted in a variety of manners, see for example FIGS. 2–8, so long as the surface area of articulation between the patellar implant 510 and the corresponding femoral component (not shown) is reduced and in accordance with the optimization of the area of the interruptions with respect to the area of the bearing surface and/or the articulation face.

An additional embodiment of the bearing component in accordance with the principles of the subject invention is illustrated in FIG. 14. A prosthetic femoral bearing component 550 is provided that is adapted to replace the extreme distal portion of a femur (not shown). The femoral portion 550 is formed to cooperate with either a natural femur or a femoral prosthetic device such as that illustrated in U.S. Pat. No. 4,822,366, the relevant portions of which are specifically incorporated herein by reference. The bearing component 550 comprises on its surface two interrupted condyles or interrupted articular surfaces 552 that are configured to replace the condyles of the distal portion of the femur (not shown). The interrupted condyles 552 minimize available surface area of articulation with either a natural tibia or a prosthetic tibial bearing component. While the illustrative bearing component is shown as being suitable for use with the tibia, it is contemplated that it may take on a form in order to cooperate with the radius and/or ulna or a radial and/or ulnar prosthesis. It should also be understood that the bearing components illustrated in FIGS. 12–15 may also be used in conjunction with the extreme distal portion of the humerus. The interrupted condyles 552 of the bearing component 550 include a smooth concave bearing surface 554 and a plurality of recesses 556 formed within the surface 554. The recesses 556 are formed as grooves or channels 558 and 560. The bearing surface 554 is defined by a plurality of bearing platforms or lands 562 integral with the face 552 and the grooves 558 and 560 that extend between the platforms 562. It should be understood that the grooves 558 and 560 may extend about the bearing surface 554 in a variety of manners, so long as the surface area of articulation between the bearing component 550 and the corresponding tibial bearing component (not shown) is reduced and in accordance with the optimization of the area of the interruptions with respect to the area of the bearing surface and/or the articulation face.

An additional embodiment in accordance with the principles of the subject invention is illustrated in FIG. 15. A tibial bearing component 750 is provided to replace the extreme proximal portion of the tibia (not shown). The tibial bearing component insert 750 comprises two interrupted slightly concave bearing surfaces 752 and 754 are adapted to support and mate with the articular surfaces on the femoral component (not shown). For a further description of the articulating movement of a prosthetic tibial bearing component insert 750 suitable for use with the subject invention, see U.S. Pat. No. 4,822,366 to Bolesky the relevant portions of which are specifically incorporated herein by reference.

An interrupted articular face 756 includes a smooth concave bearing surface 758 defined by a plurality of bearing platforms or lands 760 integral with the face 756 and a plurality of recesses 762 formed within the surface 758 between the platforms 760. Illustratively, the recesses 762 are formed as grooves or channels 764 and 766. The grooves 764 and 766 illustratively extend between the platforms 760. It should be understood that the grooves 764 and 766 may extend about the bearing surface 758 in a variety of manners, so long as the surface area of articulation between the femoral component 750 and the corresponding tibial bearing component (not shown) is reduced and in accordance with the optimization of the area of the interruptions with respect to the area of the bearing surface and/or the articulation face.

Figures 16, 17:
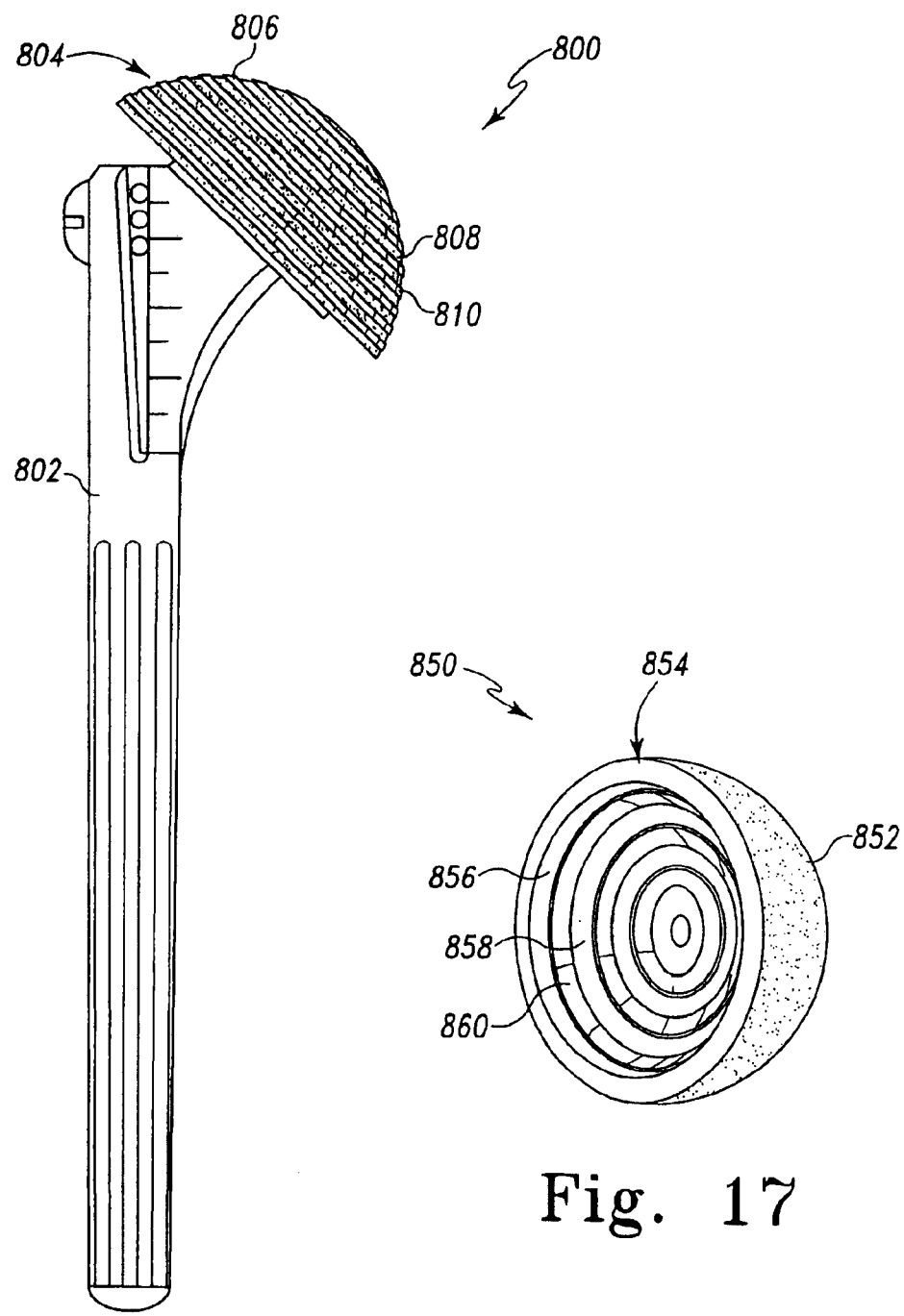
FIG. 16 is a perspective view of another exemplary embodiment of a bearing component in accordance with the principles of the subject invention showing a ball attached to a stem for a shoulder, the ball including an interrupted articular face having a bearing surface and a plurality of very fine to extremely fine intersecting grooves or channels extending into the surface.
FIG. 17 is a perspective view of an exemplary bearing component in accordance with the present invention showing a cup having an interrupted articular face having very fine to extremely fine intersecting grooves or channels extending into the surface.

FIG. 16 depicts another exemplary bearing component, here a shoulder implant generally designated 800. The shoulder implant 800 includes a stem 802 that carries a head 804. The head 804 has a bearing surface 806 that has been provided with micro-interruptions. Particularly, the head 804 has a plurality of annular micro-ring grooves or channels 808 that define a plurality of annular micro-ring lands or platforms 810. The microscopic formations are preferably on the order of less than 1 mm and more preferably in the micrometer to nanometer range. As well, the micro-interruptions may be dimples or any other micro configuration.

In FIG. 17, there is depicted another exemplary bearing component generally designated 850. The bearing component 850 is a cup/body 852 for the shoulder component 800 of FIG. 16. The bearing component body 852 defines an interior 854 that has an articular surface 856. The articular surface 856 has a plurality of micro ring grooves or channels 858 that define a plurality of annular micro-ring lands or platforms 860. The microscopic formations are preferably on the order of less than 1 mm and more preferably in the micrometer to nanometer range. As well, the micro-interruptions may be dimples or any other micro configuration.

Bearing components in accordance with the subject invention formed as acetabular sockets as shown in FIGS. 1–8 enable the to use of large ball diameters for joint stability while minimizing surface area of articulation. For example, a bearing component is manufactured for use as an acetabular socket to produce an internal diameter (herein "I.D.") of 32 mm (millimeter) with the surface area of an equivalent 28 mm I.D. component by interrupting the articular face with recesses interruptions or reliefs. Such a bearing component would have the joint stability of the 32 mm articulation and possibly the wear characteristics of the smaller I.D. It is believed that this decrease in surface area of articulation for the femoral head contributes to the reduced production of joint debris. Thus, it decreases the production of joint debris in conventional prosthetic assemblies by replacing the conventional bearing component with an improved bearing component in accordance with the principles of the subject invention having an interrupted articular face.

It should be appreciated that a 22 mm bearing component was used as a baseline to determine an appropriate optimized/adjusted bearing surface area. The optimized/adjusted bearing surface is then scaled to other sizes of the same type of prosthetic joint. It should also be appreciated that the reduced bearing surface area may be formed not only on one component of a prosthetic joint or assembly, but on both components of the prosthetic joint or assembly.

The intentional interruptions formed as grooves, channels, and/or the like as illustrated in the above embodiments may be optimized and/or adjusted for various bearing components and bearing component materials. In particular, the subject invention provides an optimum range of percentage area of relief conferred by the intentional interruptions to the bearing surface in order to provide an optimum interrupted bearing surface while maintaining optimum lubricity for a bearing component. The optimum range of interruptions is constant for a range of sizes and types of the particular bearing component and with respect to a particular material combination and clearance. It should be understood that while the following description of the subject invention is with respect to an acetabular cup assembly, the principles of the subject invention are applicable to all types of prostheses. Thus, the following analysis establishes an optimum range of percentage relief conferred by interruptions to the bearing surface of total hip implants (acetabular cup assemblies and femoral heads).

Initially, a contact mechanics equation for the particular prosthetic is established. In particular, Hertzian analysis (see Chan et al., *ASTM STP* 1346: 111–128, 1998) is used to determine the contact area, A, of metal-to-metal, ceramic-to-ceramic, and metal-to-polyethylene bearing components for a total hip arthroplasty as follows:

$$A = \pi a^2 = \pi [(3FR/2E')^{1/3}]^2$$

where:

$R = (R_C R_H)/(R_C - R_H)$; and $1/E' = (1 - v_1^2/2E_1) + (1 - v_2^2/2E_2)$; and where a = Radius of Hertzian contact area (m);

$E_n$ = Modulus of elasticity of material n (Pa);

E' = Effective modulus of elasticity (Pa);

F = Total load (N)

R = Effective Radius (m);

$R_c$ = Radius of acetabular cup (m)

$R_h$ = Radius of femoral head (m)

$v_n$ = Poisson's ration of material n.

For these calculations, a maximum force, F, of 2100 N (approximately three body weights) (see Davy et al., *JBJS-A* 1: 45-5-, 1998) and general mechanical properties (as summarized in Table 1 below) were used to determine the maximum contact area.

TABLE 1

|  | Metal (Cobalt Chromium) | Ceramic (Alumina or Zirconia) | Polyethylene |
| --- | --- | --- | --- |
| E (Pa) | 210 · 10⁹ | 350 · 10⁹ | 500 · 10⁶ |
| v | 0.3 | 0.3 | 0.46 |

For each material combination, the contact area of an appropriate low-wearing bearing was calculated. The premise of the subject invention is to define the contact area of an appropriate low-wearing bearing as the ideal or baseline contact area for each bearing combination and for a range of component (here femoral head or articulating surface of acetabular cup) diameters relevant to total hip arthroplasty. The baseline contact area was maintained for different diameters by intentionally interrupting the otherwise continuous bearing surface of the bearing component by features including but not limited to grooves or channels on either a micro or macro scale such as those shown and described herein. These features can be on either of the bearing component of the particular prosthesis (here either the femoral head or the acetabular cup).

In achieving a specific baseline contact area for the bearing component, the interrupted surface area will be described as a percentage of the otherwise uninterrupted bearing surface area. The term percentage area of relief is thus defined as the percentage of the otherwise uninterrupted bearing surface area to be removed by features of the interrupted bearing surface configuration to achieve the baseline contact area.

The rationale for establishing the baseline contact area is as follows for the three bearing material combinations for an acetabular cup assembly. Metal-on-metal decreases with decreasing clearance or gap (between the prosthesis head and the prosthesis cup) (see Chan et al., *Clin Orthop* 369: 10–24, 1999; and Farrar et al., *Trans Ortho Res Soc.*: 71, 1997) and smaller diameter implants have been associated with lower friction (see Streicher et al., *Biomed Technik* 35: 107–111, 1990). Therefore, the uninterrupted bearing surface area of a 22 mm diameter metal-on-metal implant (the smallest practical implant size for an adult total hip arthroplasty) with a 40 μm diametral clearance (the smallest practical clearance given a manufacturing tolerance of ±10 μm on the head and cup inner diameter) was used as the baseline.

With regard to ceramic-on-ceramic implants, there is theoretical evidence that smaller diameter parts may be associated with lower wear (see Jin et al., *Proc Inst Mech Eng.* 211: 247–256, 1997). Therefore, the uninterrupted bearing surface area of 22 mm diameter ceramic-on-ceramic implant with a 40 μm diametral clearance was used as the baseline for ceramic-on-ceramic implants for the same reasons noted above for metal-on-metal implants.

With regard to metal-on-polyethylene, polyethylene liner wear increases with increasing component diameter (see Clarke et al., *Proc Inst Mech Eng* 211: 25–36, 1997) and with decreasing clearance (see Wang et al., *Trans Soc Biomat:*357, 1998). Therefore, the uninterrupted bearing surface area of a 22 mm diameter metal-polyethylene implant (the smallest practical implant size for adult total hip arthroplasty) with a 600 μm diametral clearance (approximately equal to a typical average nominal diametral clearance for metal to polyethylene implants was used as the baseline.

For each bearing component, the percentage area of relief, as defined above, for a given implant size to achieve the baseline contact area was calculated. An alternative representation of the interrupted surface area was determined as a percentage of the entire articular surface area (approximately by the surface area of a half-sphere with the diameter of the component). To cover the range of component size relevant for standard and surface replacement hip implants, the analysis was performed for 22 mm to 60 mm diameter components in 1 mm increments.

Figure 18:
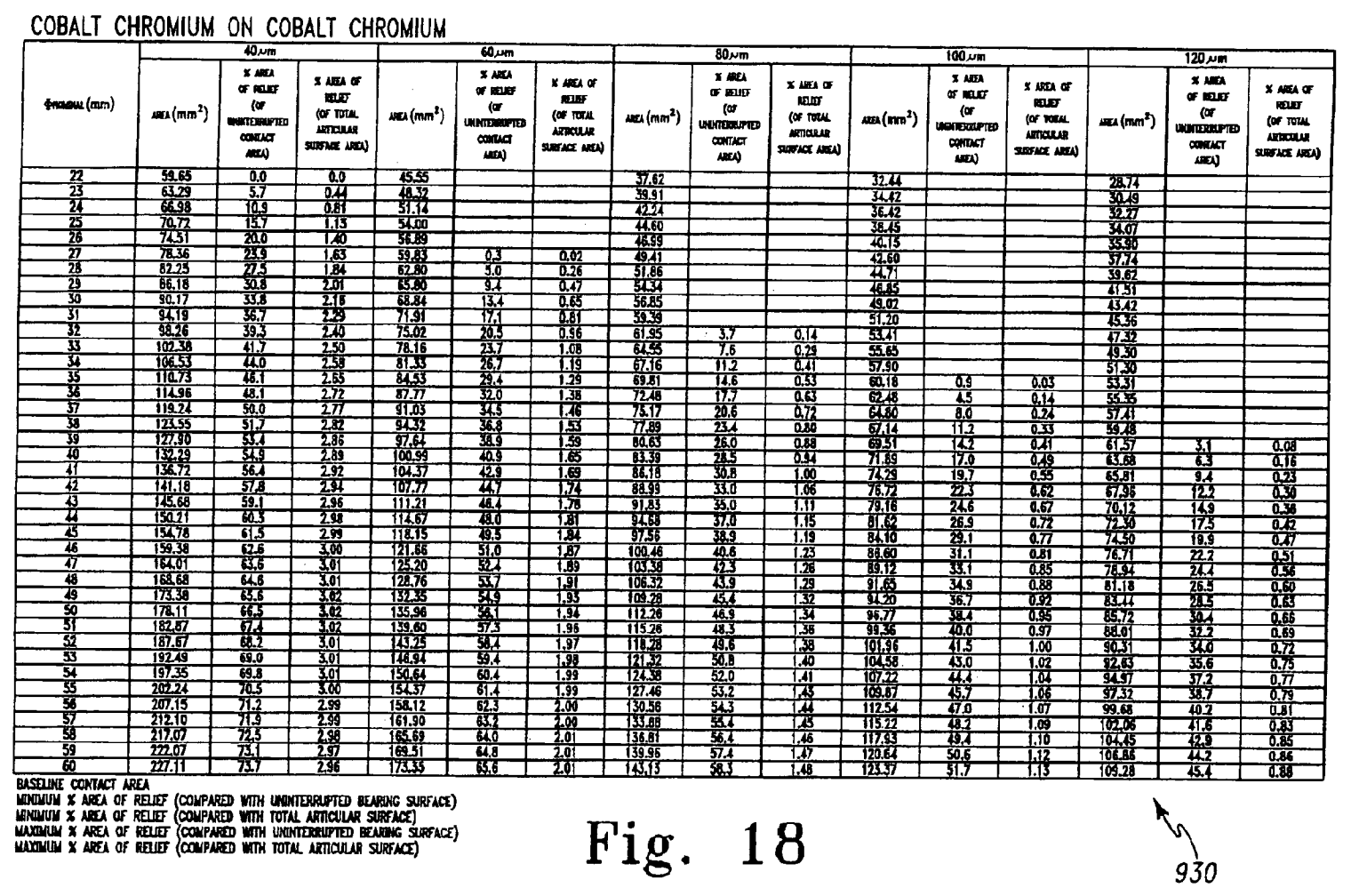
Figure 19:
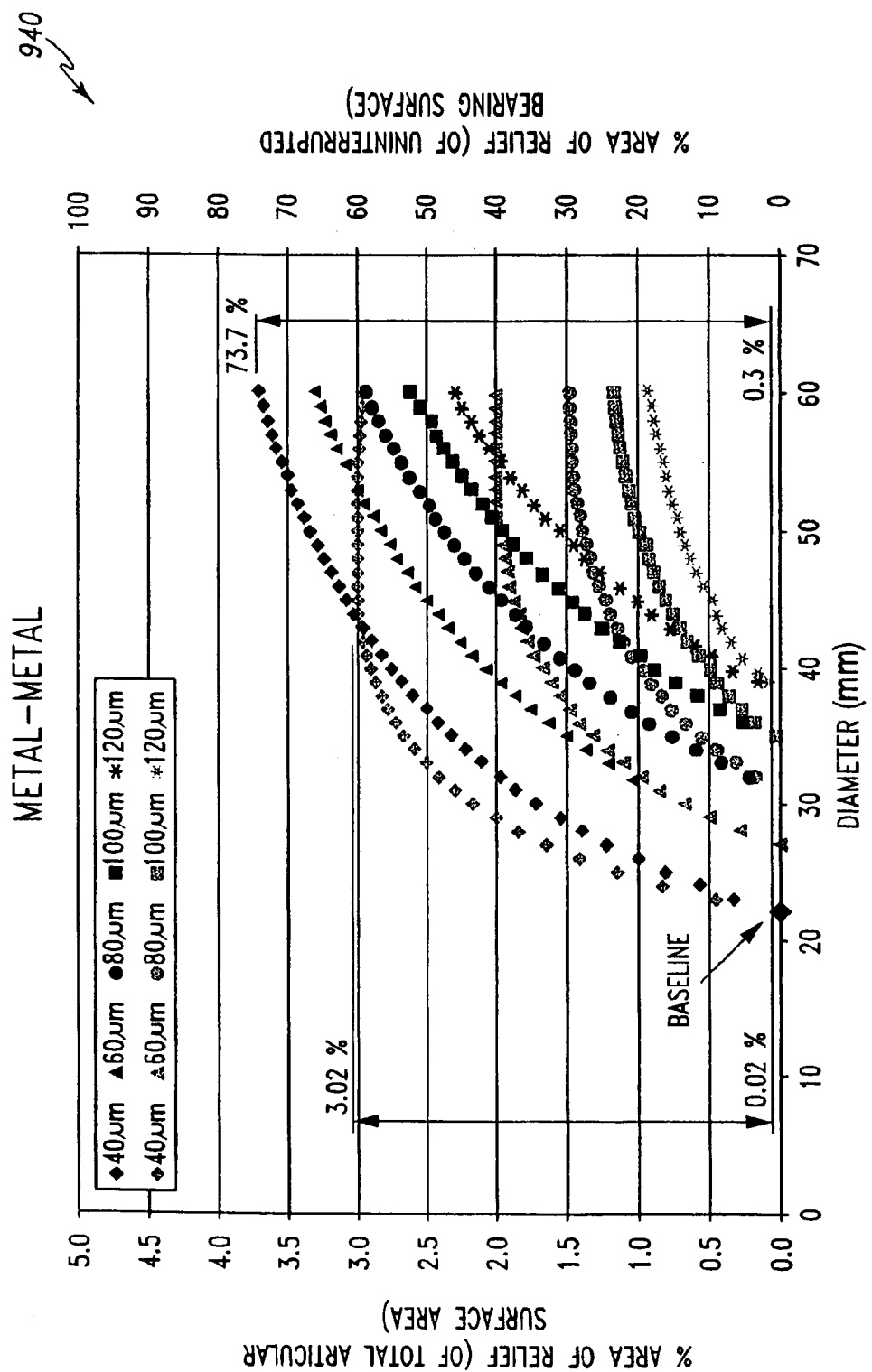
FIG. 19 is a graphical representation of the data from the table of FIG. 18.

Referring to FIG. 18, there is depicted a table, generally designated 930, that summarizes the results of the above described calculations with regard to metal-on-metal bearing components. The metal is preferably cobalt chromium but it is contemplated that other metals may be used. Particularly, table 930 shows the total area in square millimeters (mm$^2$), the percentage area of relief with regard to the uninterrupted contact area, and the percentage area of relief with regard to the total articular surface area for implants ranging from the baseline 22 mm to 60 mm in 1 mm increments for a 40 μm baseline clearance; for a 60 μm clearance; an 80 μm clearance; a 100 μm clearance; and a 120 μm clearance. Referring to FIG. 19, a graph, generally designated 940, is shown that summarizes the data from the table 930.

It can be seen from the table 930 and the graph 940 that for metal-on-metal implants with a diameter larger than that of the baseline implant, the minimum percentage of material that must be removed in the form of interruptions of the bearing surface or percentage of area of relief is (a) 0.3% of the uninterrupted bearing surface, and (b) 0.02% of the total articular surface area, to maintain the baseline contact area of 59.65 mm$^2$. As implant diameter increases, the amount of material that must be removed via interruptions of the bearing surface gradually increases to a maximum of (a) 73.7% of the uninterrupted bearing surface, and (b) 3.02% of the total articular surface area.

The following is an example utilizing the principles of the subject invention, and still referring to the table 930 of FIG. 18 and the graph 940 of FIG. 19, if one wanted to utilize a metal-on-metal implant. If one desired to fabricate a 50 mm diameter metal-metal implant with a diametral clearance of 120 μm and desired to maintain the same contact area as the baseline implant (a 22 mm diameter implant with a diametral clearance of 40 μm) a percentage area of relief would be necessary of approximately 30% of the uninterrupted bearing surface (precisely 30.4% from table 930) and approximately 0.7% of the total articular surface (precisely 0.66% from table 930) for an effective contact area of 59.65 mm$^2$.

Figure 21:
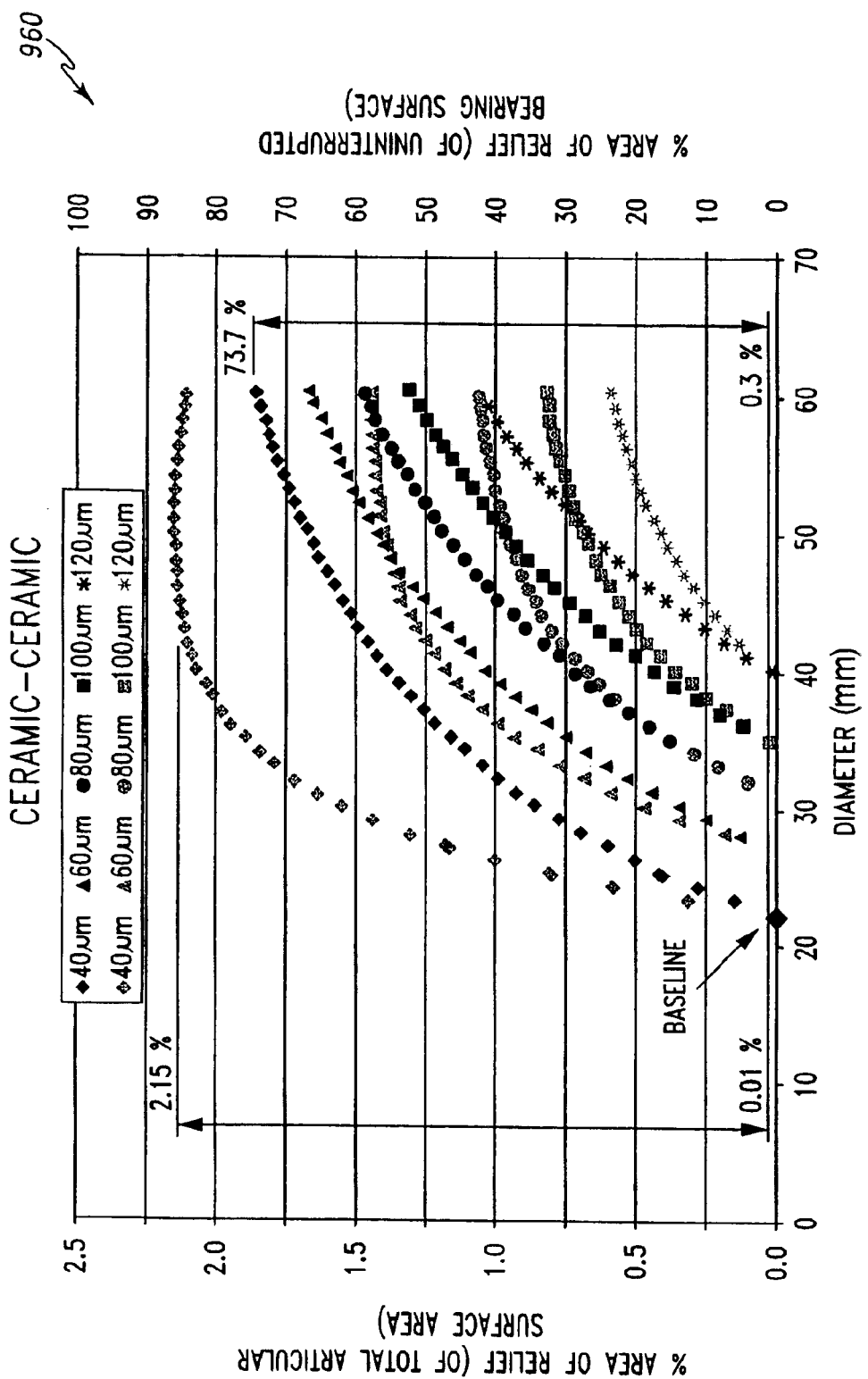
FIG. 21 is a graphical representation of the data from the table of FIG. 20.

Referring to FIG. 20, there is depicted a table, generally designated 950, that summarizes the results of the above described calculations with regard to ceramic-on-ceramic bearing components. Particularly, table 950 shows the total area in square millimeters (mm$^2$), the percentage area of relief with regard to the uninterrupted contact area, and the percentage area of relief with regard to the total articular surface area for implants ranging from the baseline 22 mm to 60 mm in 1 mm increments for a 40 μm baseline clearance; for a 60 μm clearance; an 80 μm clearance; a 100 μm clearance; and a 120 μm clearance. Referring to FIG. 21, a graph, generally designated 960, is shown that summarizes the data from the table 950.

It can be seen from the table 950 and the graph 960 that for ceramic-on-ceramic implants with a diameter larger than that of the baseline implant, the minimum percentage of material that must be removed in the form of interruptions of the bearing surface or percentage of area of relief is (a) 0.3% of the uninterrupted bearing surface, and (b) 0.01% of the total articular surface area, to maintain the baseline contact area of 42.43 mm$^2$. As implant diameter increases, the amount of material that must be removed via interruptions of the bearing surface gradually increases to a maximum of (a) 73.7% of the uninterrupted bearing surface, and (b) 2.15% of the total articular surface area.

The following is an example utilizing the principles of the subject invention, and still referring to the table 950 of FIG. 20 and the graph 960 of FIG. 21, if one wanted to utilize a ceramic-on-ceramic implant. If one desired to fabricate a 37 mm diameter ceramic-ceramic implant with a diametral clearance of 80 μm and desired to maintain the same contact area as the baseline implant (a 22 mm diameter implant with a diametral clearance of 40 μm) a percentage area of relief would be necessary of approximately 21% of the uninterrupted bearing surface (precisely 20.6% from table 950) and approximately 0.5% of the total articular surface (precisely 0.51% from table 950) for an effective contact area of 42.43 mm$^2$.

Figure 23:
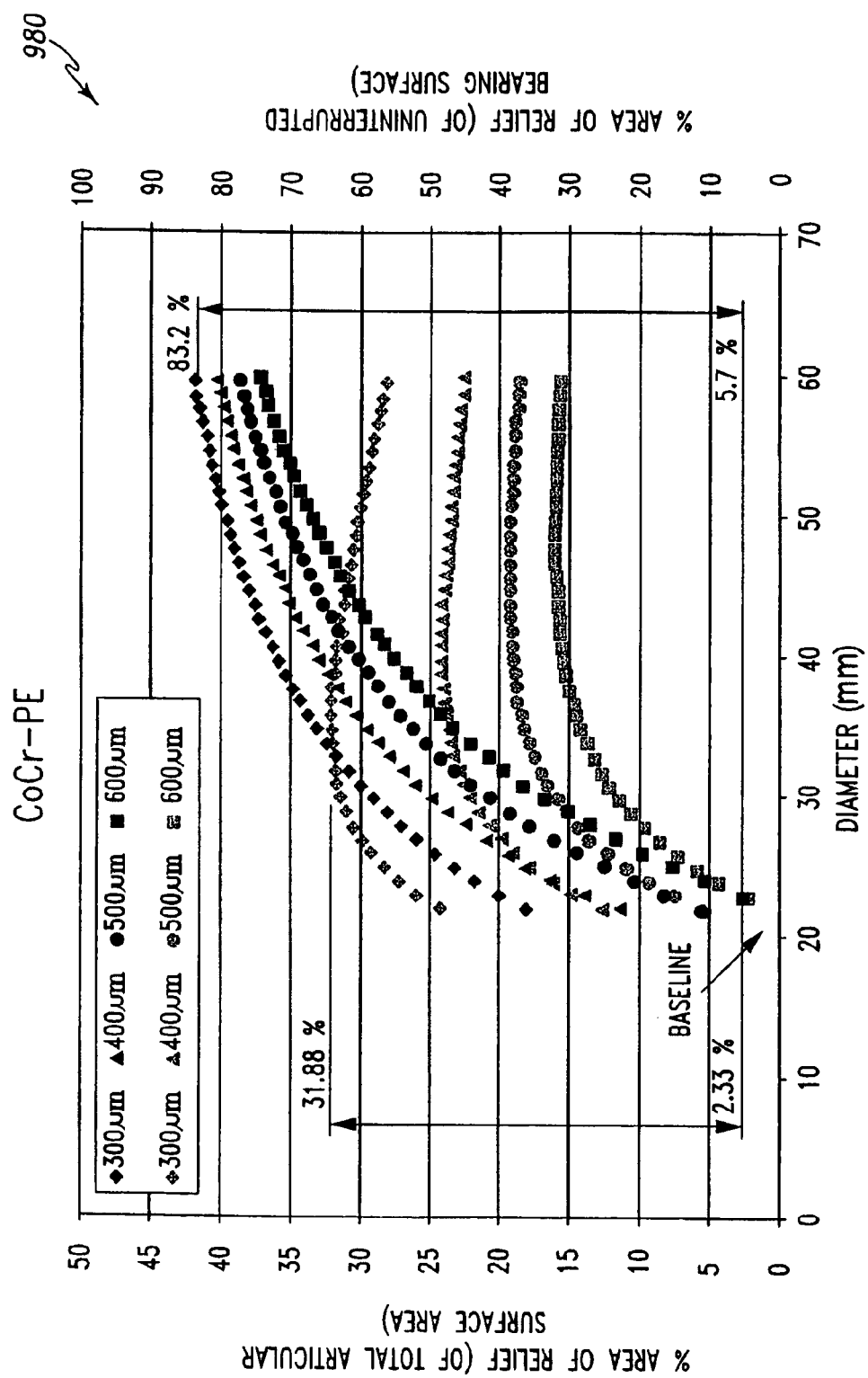
FIG. 23 is a graphical representation of the data from the table of FIG. 22.

Referring to FIG. 22, there is depicted a table, generally designated 970, that summarizes the results of the above described calculations with regard to metal-on-polyethylene bearing components. The metal is preferably cobalt chromium but it is contemplated that other metals may be used. Particularly, table 970 shows the total area in square millimeters (mm$^2$), the percentage area of relief with regard to the uninterrupted contact area, and the percentage area of relief with regard to the total articular surface area for implants ranging from the baseline 22 mm to 60 mm in 1 mm increments for a 300 μm baseline clearance; for a 400 μm clearance; a 500 μm clearance; and a 600 μm clearance. Referring to FIG. 23, a graph, generally designated 980, is shown that summarizes the data from the table 970.

It can be seen from the table 970 and the graph 980 that for metal-on-polyethylene implants with a diameter larger than that of the baseline implant, the minimum percentage of material that must be removed in the form of interruptions of the bearing surface or percentage of area of relief is (a) 5.7% of the uninterrupted bearing surface, and (b) 2.33% of the total articular surface area, to maintain the baseline contact area of 504.69 mm². As implant diameter increases, the amount of material that must be removed via interruptions of the bearing surface gradually increases to a maximum of (a) 83.2% of the uninterrupted bearing surface, and (b) 31.88% of the total articular surface area.

The following is an example utilizing the principles of the subject invention, and still referring to the table 970 of FIG. 22 and the graph 980 of FIG. 23, if one wanted to utilize a metal-on-polyethylene implant. If one desired to fabricate a 46 mm diameter metal-polyethylene implant with a diametral clearance of 400 μm and desired to maintain the same contact area as the baseline implant (a 22 mm diameter implant with a diametral clearance of 300 μm) a percentage area of relief would be necessary of approximately 71% of the uninterrupted bearing surface (precisely 71.1% from table 970) and approximately 24% of the total articular surface (precisely 23.75% from table 970) for an effective contact area of 320.78 mm².

The above results are summarized in Table 2, below:

TABLE 2

| | | Metal—Metal | Ceramic—Ceramic | Metal-Polyethylene |
|---|---|---|---|---|
| Baseline | Description of Implant | φ = 22 mm, $C_d$ = 40 μm | φ = 22 mm, $C_d$ = 40 μm | φ = 22 mm, $C_d$ = 600 μm |
| | Contact Area (mm²) | 59.65 | 42.43 | 320.78 |
| % Area of Relief Relative to Uninterrupted Contact Area | Minimum | 0.3 | 0.3 | 5.7 |
| | Maximum | 73.7 | 73.7 | 83.2 |
| % Area of Relief Relative to Total Articular Surface Area | Minimum | 0.02 | 0.01 | 2.33 |
| | Maximum | 3.02 | 2.15 | 31.88 |

It should be appreciated that the term "otherwise uninterrupted bearing surface area" is the region of intimate contact between two bodies or components. The interruptions can be on either component or both components as long as the desired contact area as calculated herein is maintained. The term "total articular surface area" is essentially the total region where contact is possible for the two components. This area would thus necessarily be the lesser of the possible area on either the head or cup (two components of the assembly such as a joint). The total articular surface area is thus typically the surface area of the component.

Although the invention has been described in detail with reference to certain preferred embodiments, variations and modifications exist within the scope and spirit of the invention as described and defined in the following claims. For example, while the prosthetic cup assembly is disclosed in the context of a hip prosthesis, it has utility in other locations within a patient's body.

What is claimed is:

1. A method of making a prosthetic joint, comprising the steps of:

determining a clearance distance between (i) a first articular surface of a first component of said prosthetic joint, and (ii) a second articular surface of a second component of said prosthetic joint;

deriving a baseline contact area value for said first articular surface and said second articular surface; and forming interruptions in both said first articular surface and said second articular surface based on said baseline contact area value.

2. The method of claim 1, wherein the step of deriving said baseline contact area value includes the step of performing Hertzian analysis.

3. The method of claim 2, wherein the step of performing Hertzian analysis includes the step of applying contact mechanic equations.

4. The method of claim 2, wherein the step of deriving a baseline contact area value includes calculating a contact area of a low-wearing prosthetic joint.

5. The method of claim 1, wherein said forming step in includes the step of forming said interruptions in both said first articular surface and said second articular surface to a depth of less than one millimeter.

6. The method of claim 1, wherein:

said first component is formed of a first material, said second component is formed of a second material, and said first material is different from said second material.

7. The method of claim 6, wherein:

said first material includes metal, and said second material includes plastic.

8. The method of claim 7, wherein said plastic includes a polyethylene material.

9. The method of claim 7, wherein said metal includes cobalt chromium.

10. The method of claim 1, wherein:

said first material includes metal, and said second material includes metal.

11. The method of claim 10, wherein said metal includes cobalt chromium.

12. The method of claim 1, wherein:

said first material includes ceramic, and said second material includes ceramic.

13. The method of claim 12, wherein said ceramic is selected from the group consisting of: alumina and zirconia.

* * * * *